United States Patent [19]
Heath et al.

[11] Patent Number: 5,106,298
[45] Date of Patent: Apr. 21, 1992

[54] ENDODONTIC DENTAL INSTRUMENT

[76] Inventors: Derek E. Heath, 1917 Sherwood Dr., Johnson City, Tenn. 37604; Jerry A. Mooneyhan, 711 N. Mountainview Cir., Johnson City, Tenn. 37601

[21] Appl. No.: 679,628

[22] Filed: Apr. 3, 1991

[51] Int. Cl.⁵ .............................................. A61C 5/02
[52] U.S. Cl. .................................................. 433/102
[58] Field of Search ............................... 433/102, 224

[56] References Cited

U.S. PATENT DOCUMENTS

| | | | |
|---|---|---|---|
| 1,067,015 | 8/1913 | Fowler | 433/102 |
| 1,307,446 | 6/1919 | Kerr | |
| 1,694,857 | 12/1928 | Kulik | 433/81 |
| 3,924,334 | 12/1975 | Lentine et al. | 433/102 |
| 4,299,571 | 11/1981 | McSpadden | 433/102 |
| 4,332,561 | 6/1982 | McSpadden | 433/102 |
| 4,353,698 | 10/1982 | McSpadden | 433/164 |
| 4,443,193 | 4/1984 | Roane | 433/102 |
| 4,457,710 | 7/1984 | McSpadden | 433/81 |
| 4,538,989 | 9/1985 | Apairo, Jr. et al. | 433/102 |
| 4,871,312 | 10/1989 | Heath | 433/164 |
| 4,934,934 | 6/1990 | Arpaio, Jr. et al. | 433/102 |

FOREIGN PATENT DOCUMENTS

| | | |
|---|---|---|
| 279144 | 10/1913 | Fed. Rep. of Germany . |
| 365050 | 12/1922 | Fed. Rep. of Germany . |
| 2724516 | 4/1978 | Fed. Rep. of Germany . |
| 775073 | 12/1934 | France . |

Primary Examiner—Gene Mancene
Assistant Examiner—Cindy A. Cherichetti
Attorney, Agent, or Firm—Bell, Seltzer, Park & Gibson

[57] ABSTRACT

An endodontic instrument is disclosed which comprises an elongate shank having a lower working length. One or more helical flutes are positioned on the working length, and the bottoms of the flutes define a solid core which is cylindrical in one embodiment, and reversely tapered in another embodiment. The solid core permits the working length to permanently twist upon becoming locked in the canal during root canal therapy, and the twists move upwardly from the point of locking engagement until they may be visually and/or tactilely noted by the dentist, and so that the dentist is alerted before breakage occurs.

16 Claims, 1 Drawing Sheet

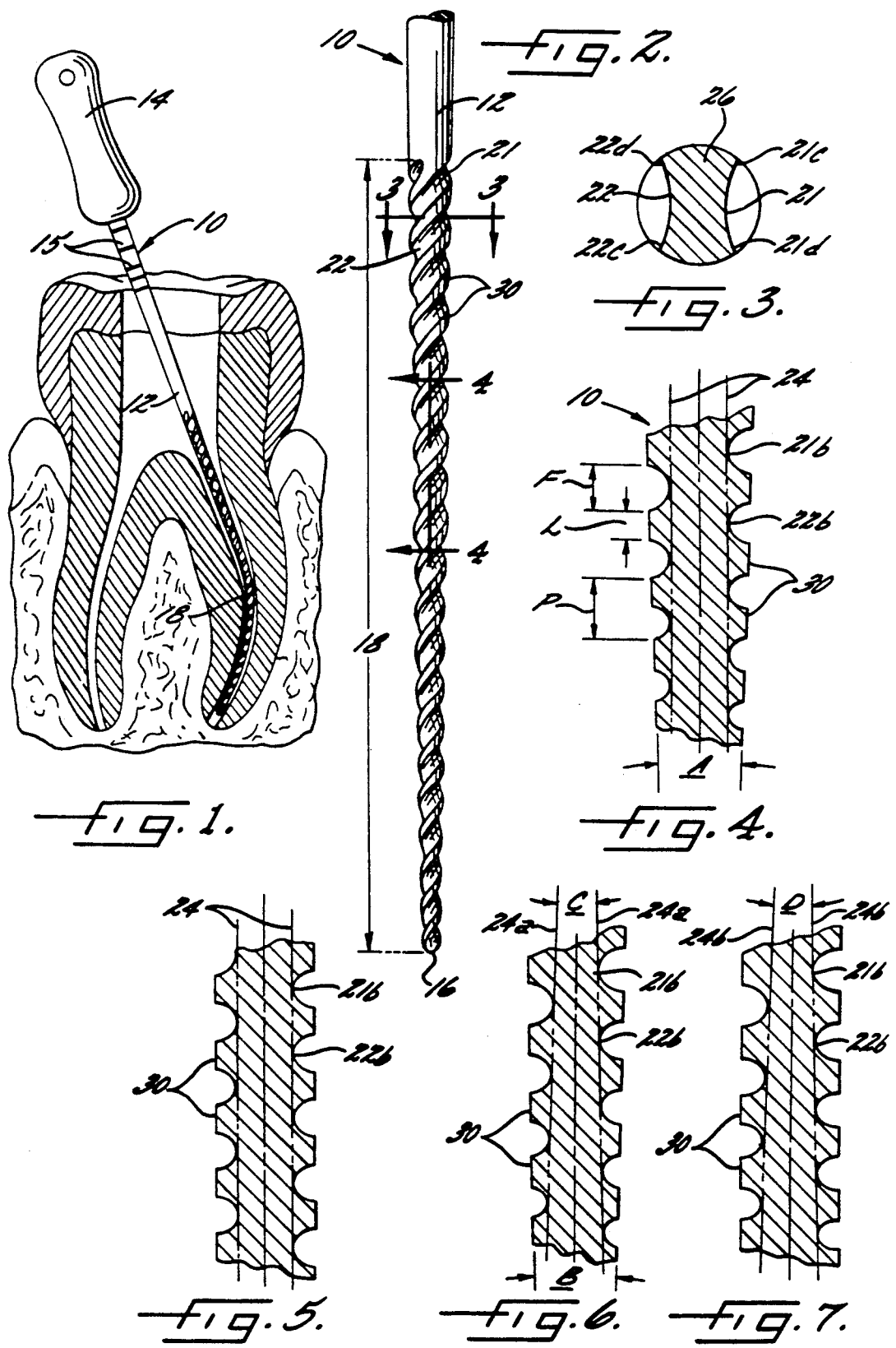

ENDODONTIC DENTAL INSTRUMENT

BACKGROUND OF THE INVENTION

The present invention relates to an endodontic instrument adapted for use in performing root canal therapy on teeth.

Root canal therapy is a well-known procedure wherein the crown of the diseased tooth is opened so as to permit the canal to be cleaned and then filled. More particularly, a series of very delicate, flexible, finger held instruments or files are used to clean out and shape the root canal, and each file is manually rotated and reciprocated in the canal by the dentist. Files of increasingly larger diameter are used in sequence, to achieve the desired cleaning and shaping. When the canal is thus prepared, it is solidly filled with a filling material, which typically comprises a waxy, rubbery compound known as gutta percha. In one procedure, the gutta percha is positioned on an instrument called a compactor, and the coated compactor is inserted into the prepared canal and rotated and reciprocated to compact the gutta percha therein. The dentist thereafter fills the tooth above the gutta percha with a protective cement, and lastly, a crown may be fitted to the tooth.

A file of the described type is illustrated in U.S. Pat. No. 4,934,934, and a compactor of the described type is illustrated in U.S. Pat. No. 4,871,312. In each case, the instrument typically comprises a stainless steel shank having one or more helical flutes formed in the working portion of the shank.

A major problem associated with conventional endodontic instruments used in performing root canal therapy, is the fact that the instruments easily break while in the canal as a result of the rotating and reciprocating movement. More particularly, the instrument often engages and locks at a location adjacent the bottom end of the canal, such that continued rotation and reciprocation result in its breakage at a point adjacent the locking point. Upon breakage, a remnant of the instrument remains in the lower portion of the canal and it is difficult and often impossible to remove the remnant. If the remnant can not be removed, it is sometimes necessary to extract the tooth.

It is accordingly an object of the present invention to provide an endodontic instrument which is adapted for use in performing root canal therapy, and which is resistant to breakage during the procedure.

It is a more particular object of the present invention to provide an endodontic instrument of the described type, and which provides the dentist with a visual and/or tactile indication that it is about to break, thereby providing an opportunity to terminate the procedure before breakage, and so that a new instrument may be substituted for the weakened instrument.

SUMMARY OF THE INVENTION

The above and other objects and advantages of the present invention are achieved in the embodiments illustrated herein by the provision of an endodontic instrument which comprises an elongate shank having a proximate end and an opposite pilot end, and a working length adjacent the pilot end. At least one continuous helical flute is formed so as to extend along the length of the working length, with each of the flutes having a base at the point of maximum depth from the peripheral surface of the working length, and with the base of each of the flutes defining a solid core which is substantially cylindrical or tapered toward the proximate end when viewed in longitudinal cross section.

The present invention involves the discovery that with the prior instruments, the above defined solid core of the shaft typically tapers toward the pilot end, since the external peripheral surface is usually tapered and the flutes are of uniform depth. As a result, the weakest portion of the shank is adjacent the pilot end, and upon the pilot end becoming locked in the canal, the shaft will tend to break adjacent the point at which it is locked, i.e. adjacent the pilot end. Thus the broken remnant is commonly out of reach and cannot be removed.

In accordance with the present invention, it has been discovered that by making the core of the working length in the form of a cylinder, or reversely tapered toward the handle of the shank, the strength along the length of the working length may be significantly increased so as to resist breakage. In addition, and unexpectedly, the fact that the core is cylindrical or reversely tapered causes the shaft to "wind-up", i.e. form permanent twists, upon the working length becoming locked in the bottom end of the canal during manipulation by the dentist, and the twists progress upwardly toward the handle of the instrument from the binding point in the canal as the manipulation by the dentist proceeds. The resulting twists may be visually and/or tactilely noted by the dentist and thus they provide an indication that the shaft is about to break. Further, in the event breakage does occur, it will likely occur where the twists reach the solid, non-fluted proximate end portion of the shank. As a result, it is likely that the remnant of the broken shaft can be gripped and removed from the canal.

BRIEF DESCRIPTION OF THE DRAWINGS

Some of the objects and advantages of the present invention having been stated, others will appear as the description proceeds, when taken in conjunction with the accompanying drawings, in which FIG. 1 is a sectional view of a tooth having two roots, with an endodontic instrument which embodies the present invention received in one of the roots;

FIG. 2 is an enlarged perspective view of the lower portion of the instrument shown in FIG. 1;

FIG. 3 is a transverse sectional view taken substantially along the line 3—3 of FIG. 2;

FIG. 4 is a longitudinal sectional view taken substantially along the line 4—4 of FIG. 2;

FIG. 5 is a view similar to FIG. 4 but illustrating a further embodiment wherein the outer peripheral surface of the pilot end portion of the shank, and the core are both in the form of a cylinder;

FIG. 6 is a view similar to FIG. 4 but illustrating another embodiment wherein the external surface of the pilot end portion is tapered toward the pilot end, while the core is reversely tapered; and FIG. 7 is a view similar to FIG. 4 but illustrating still another embodiment wherein the outer peripheral surface of the pilot end portion is cylindrical, and the core is reversely tapered.

DETAILED DESCRIPTION OF THE PREFERRED EMBODIMENTS

Referring more particularly to FIGS. 1-4, an endodontic instrument 10 is illustrated which comprises a shank 12 which is preferably composed of a metallic material such as stainless steel, and which is of circular cross-sectional configuration. The shank 12 typically has a length of about 30 mm (1.2 inches), and it includes an outer or proximate end which mounts a conventional handle 14, and the portion of the shank immediately below the handle includes calibrated depth markings 15 of conventional design. The shank further includes an opposite distal or pilot end 16, and a tapered working length 18 is defined adjacent the pilot end 16. The working length 18 may have a length of from about 2 mm (0.08 inches) up to the full length of the shank 12, i.e. about 30 mm (1.2 inches). However, in the illustrated embodiment, the working length 18 has a length sufficient to extend substantially the full depth of a tooth root canal as illustrated in FIG. 1, which is about 16 mm (0.63 inches).

The outer peripheral surface of the working length 18 is tapered, so as to define an included angle A of between about ½ and 4 degrees, and preferably about 1 degree, note FIG. 4. Also, in the illustrated embodiment, the working length 18 includes two continuous helical flutes 21, 22 formed in the peripheral surface, and as best seen in FIG. 4, each of the flutes 21, 22 is arcuately curved and defines a bottom or base 21b, 22b, respectively, at the point of maximum depth from the peripheral surface. The bases 21b, 22b of the two flutes define a solid cylindrical core, which is represented by the broken lines 24 in FIG. 4. Stated in other words, the depth of the flutes 21, 22 increases from the pilot end 16 toward the proximate end at the handle 14, and the increase in the depth is sufficient to form a cylindrical core.

As best seen in FIG. 3, which is a transverse cross-sectional view of the pilot end portion of the shank, the two flutes 21, 22 define a web 26 therebetween. In addition, each of the flutes defines a curved concave wall when viewed in transverse cross-section, and each wall includes a pair of helical shoulders 21c, 21d and 22c, 22d, at the peripheral surface and which face in generally opposite axial directions. The shoulders 21c, 21d, 22c, 22d each intersect the periphery of the shank at an angle of about 90° to a tangent to the shank at the point of intersection, to form what is commonly referred to as a substantially zero or neutral rake angle. Stated in other words, each shoulder lies substantially on a radius of the shank as seen in FIG. 3.

The peripheral surface of the working length 18 comprises a helical land 30 which is positioned between axially adjacent flute segments.

The flutes are preferably of uniform pitch P (FIG. 4), which is defined herein as the distance between corresponding points of adjacent flute segments. In a typical example, the length of the working length 18 is about 0.63 inches, with a total of about 18 flute spirals extending along the entire length of the pilot end portion, such that the pitch P is 0.63/18 or about 0.035 inches. Since the depth of the flutes varies as described above, the width F of the flutes, and the width L of the lands 30 will inversely vary somewhat along the length of the pilot end portion. For example, in the above example, the width F of the flutes is about 0.03 inches and the width L of lands 30 is about 0.005 inches at the upper end of the working length adjacent the handle 14, and the width W is about 0.025 inches and the width L is about 0.01 inches adjacent the pilot end 16. As will be apparent, the width L of the lands 30 is equal to a significant portion of the pitch P, which is preferably equal to at least about 15% of the pitch P. In the above example, the width L varies from about 14.2% of the pitch P adjacent the upper end to about 28.5% of the pitch P adjacent the pilot end 16. This is desirable in that the relatively broad lands 30 prevent undue cutting by the instrument laterally into the wall of the canal during manipulation of the instrument by the dentist.

FIG. 5 illustrates another embodiment of the invention, which is similar to the above described embodiment, with the exception that the peripheral surface of the working length is cylindrical rather than tapered.

FIG. 6 illustrates another embodiment where the peripheral surface of the working length is tapered toward the pilot end as indicated by the included angle B, which corresponds in angle to that described above for the angle A of the embodiment of FIGS. 1-4. The core is represented by the broken lines 24a, and it is reversely tapered as indicated by the included angle C, which is typically between about ½ and 4 degrees.

FIG. 7 illustrates still another embodiment, wherein the outer peripheral surface is substantially cylindrical, but the core, as represented by the broken lines 24b, is reversely tapered as indicated by the included angle D, which is typically between about ½ and 4 degrees.

In all of the embodiments of the invention, the fact that the core is cylindrical as in the embodiments of FIGS. 1-5, or reversely tapered as seen in the embodiments of FIGS. 6-7, has been found to permit the working length to wind-up, or permanently twist, when the instrument becomes locked in the canal during manipulation by the dentist. The resulting permanent twists move upwardly along the shaft from the point of locking engagement, and the twists eventually reach an elevation where they can be visually or tactilely noted by the dentist. The dentist is thereby alerted that the instrument is about to break, and it can be removed and replaced.

In the embodiments of FIGS. 6 and 7, it will be noted that the diameter of the core decreases as the distance from the pilot end 16 increases, thereby rendering the upper portion of the working length relatively weak. This has the further advantage that in the event of breakage, it would most likely occur in the upper portion of the working length, so that the remnant may be gripped and removed from the canal.

In the drawings and specification, there has been set forth a preferred embodiment of the invention, and although specific terms are employed, they are used in a generic and descriptive sense only and not for purposes of limitation.

That which is claimed is:

1. An endodontic instrument adapted for use in performing root canal therapy on a tooth, and comprising an elongate shank having a proximate end and an opposite pilot end, and so as to define a working length adjacent said pilot end which includes a peripheral surface, and wherein said peripheral surface is tapered toward said pilot end at an included angle of between about ½ and 4 degrees, and at least one continuous helical flute formed so as to extend along the length of said working length, with each of said flutes having a base at the point of maximum depth from the peripheral surface of said working length, and with said base of each of said flutes defining a solid core which is substantially cylindrical, and wherein said peripheral surface of said working length comprises a helical land which is positioned between axially adjacent flute segments, and with said helical land having a width which is equal to at least about 15% of the pitch of said helical flutes when viewed in longitudinal cross section.

2. The endodontic instrument as defined in claim 1 wherein each of said helical flutes defines a curved concave wall when viewed in transverse cross section.

3. The endodontic instrument as defined in claim 2 wherein each of said flutes defines a pair of helical shoulders at the peripheral surface of said pilot end portion and which face in generally opposite axial directions, and wherein each of said helical shoulders of each of said flutes has a substantially neutral rake angle.

4. The endodontic instrument as defined in claim 1 further comprising a handle mounted at said proximate end of said shank.

5. The endodontic instrument as defined in claim 1 wherein said helical land lies along an arc of a circle when viewed in transverse cross section.

6. An endodontic instrument adapted for use in performing root canal therapy on a tooth, and comprising
an elongate shank having a proximate end and an opposite pilot end, and so as to define a working length adjacent said pilot end which includes a peripheral surface which is tapered toward said pilot end at an included angle of between about ½ and 4 degrees, and
at least one continuous helical flute formed so as to extend along the length of said working length, with each of said flutes having a base at the point of maximum depth from said peripheral surface of said working length, and with said base of each of said flutes defining a solid core which is tapered toward said proximate end at an included angle of between about ½ and 4 degrees when viewed in longitudinal cross section.

7. An endodontic instrument adapted for use in performing root canal therapy on a tooth, and comprising
an elongate shank having a proximate end and an opposite pilot end, and so as to define a working length adjacent said pilot end which includes a peripheral surface, and wherein said peripheral surface is tapered toward said pilot end at an included angle of between about ½ and 4 degrees, and
at least one continuous helical flute formed so as to extend along the length of said working length, with each of said flutes having a base at the point of maximum depth from the peripheral surface of said working length, and with said base of each of said flutes defining a solid core which is tapered toward said proximate end at an included angle of between about ½ and 4 degrees when viewed in longitudinal cross section, and wherein said peripheral surface of said working length comprises a helical land which is positioned between axially adjacent flute segments, and with said helical land having a width which is equal to at least about 15% of the pitch of said helical flutes when viewed in longitudinal cross section.

8. The endodontic instrument as defined in claim 7 wherein each of said helical flutes defines a curved concave wall when viewed in transverse cross section.

9. The endodontic instrument as defined in claim 8 wherein each of said flutes defines a pair of helical shoulders at the peripheral surface of said pilot end portion and which face in generally opposite axial directions, and wherein each of said helical shoulders of each of said flutes has a substantially neutral rake angle.

10. The endodontic instrument as defined in claim 7 further comprising a handle mounted at said proximate end of said shank.

11. The endodontic instrument as defined in claim 7 wherein said helical land lies along an arc of a circle when viewed in transverse cross section.

12. An endodontic instrument adapted for use in performing root canal therapy on a tooth, and comprising
an elongate shank having a proximate end and an opposite pilot end, and so as to define a working length adjacent said pilot end which includes a substantially cylindrical peripheral surface, and
at least one continuous helical flute formed so as to extend along the length of said working length, with each of said flutes having a base at the point of maximum depth from the peripheral surface of said working length, and with said base of each of said flutes defining a solid core which is tapered toward said proximate end at an included angle of between about ½ and 4 degrees when viewed in longitudinal cross section, and wherein said peripheral surface of said working length comprises a helical land which is positioned between axially adjacent flute segments, and with said helical land having a width which is equal to at least about 15% of the pitch of said helical flutes when viewed in longitudinal cross section.

13. The endodontic instrument as defined in claim 12 wherein each of said helical flutes defines a curved concave wall when viewed in transverse cross section.

14. The endodontic instrument as defined in claim 13 wherein each of said flutes defines a pair of helical shoulders at the peripheral surface of said pilot end portion and which face in generally opposite axial directions, and wherein each of said helical shoulders of each of said flutes has a substantially neutral rake angle.

15. The endodontic instrument as defined in claim 12 further comprising a handle mounted at said proximate end of said shank.

16. The endodontic instrument as defined in claim 12 wherein said helical land lies along an arc of a circle when viewed in transverse cross section.

* * * * *